United States Patent [19]

Usdin et al.

[11] 4,145,413

[45] Mar. 20, 1979

[54] ARTIFICIAL SKIN DARKENING COMPOSITION AND METHOD OF USING THE SAME

[75] Inventors: Vera R. Usdin, Arlington, Va.; Edwin Kaszynski, Wheaton, Md.

[73] Assignee: The Gillette Company, Boston, Mass.

[21] Appl. No.: 824,792

[22] Filed: Aug. 15, 1977

[51] Int. Cl.$^2$ .................. A61K 7/021; A61K 7/42
[52] U.S. Cl. .................................. 424/63; 8/10.1; 424/47; 424/362
[58] Field of Search ............... 424/63, 47; 8/10.1, 8/10.2

[56] References Cited

U.S. PATENT DOCUMENTS 3,402,986  9/1968  Zviak et al. .................. 8/10.1

3,480,377  11/1969  Lyons ........................ 8/10.1

OTHER PUBLICATIONS

Pharm. Formulas, 1947, 10th Ed., pp. 784, 785, 790, 791, 799–801, 804, 806, 823.
Chem. Abs., 1951, vol. 45, p. 5047.
Harry, Modern Cosmeticology, 1947, pp. 318–322.
Redgrove Hair Dyes & Hair Dyeing, 1939, pp. 61–64, 67–69, 76, 77, 79, 80, 323–325.
Goodman, Cosmetic Dermatology, 1937, pp. 527–528.

*Primary Examiner*—Dale R. Ore
*Attorney, Agent, or Firm*—Richard A. Wise

[57] ABSTRACT

Skin darkening compositions are made by dissolving cuprous chloride and either benzyl alcohol or 2,3-dihydroxybenzoic acid in an aqueous dermatologic base.

6 Claims, No Drawings

ARTIFICIAL SKIN DARKENING COMPOSITION AND METHOD OF USING THE SAME

FIELD OF THE INVENTION

This invention relates to cation/carrier solvent systems useful in the formulation of skin darkening compositions.

BACKGROUND OF THE INVENTION

In our present society, a glowing suntan is frequently equated with a healthy, athletic life style and the means to pursue it on a year-round basis. However, the acquisition of a natural tan may not only be time consuming but almost impossible for those very light skinned persons who tend to burn rather than tan. In addition, the deleterious effects of excessive exposure to sunlight are becoming more generally recognized. One of the most common methods for artificially inducing a suntan is to subject the body to the rays of an ultraviolet ray lamp. While this induces a tan similar to the sun, it has many of the same disadvantages as tanning by the sun since many of the deleterious effects of sunlight are due to its U.V. radiation component. For instance, the increasing incidence of skin cancer has been attributed to increased exposure to U.V. radiation from the sun.

For these and other reasons, there is a perceived need for topically applied materials which simulate the appearance of a tan and, at the same time, protect the skin from U.V. induced damage.

The first step in any attempt to find such a material is to identify the exact effect desired. A suntan is really a combination of a brown coloration resulting from increased melanin synthesis, and a red coloration resulting from mild erythema if the exposure has been kept in the prudent range.

The material should be non-toxic and non-irritating, easy to apply, and stable in dermatologically acceptable formulations. The color produced on the skin should last for several days and be resistant to run-off and wash-off.

While dihydroxyacetone, which has been widely commercialized as a skin tanning agent, produces a brown coloration, it suffers from a number of problems. As mentioned above, a natural suntan has a reddish tint due to erythema. One attempt to remedy this shortcoming in dihydroxyacetone compositions involves the addition of alloxan which yields a pinkish-red color with proteins and peptides. Some commercial dihydroxyacetone preparations have contained up to 50% alcohol. Such alcoholic preparations tend to dry the skin. To overcome this, attempts have been made to use "creamy bases" such as are found in hand and face lotions, and cold creams. But dihydroxyacetone decomposes if any amino groups are present in the cream with a resulting loss in tanning ability. This limits the number of such cosmetic bases that may be used. Finally, due to dihydroxyacetone's reactivity toward amino groups, the types and thus number of sunscreens which may be used in conjunction with it are limited. Due to the negative attributes of dihydroxyacetone, the search for other artificial tanning agents has continued.

We have discovered that aqueous solutions containing cuprous ion and either benzyl alcohol or 2,3-dihydroxybenzoic acid produce a golden brown color closely resembling the color of a natural suntan when applied to the skin. Furthermore, these compositions are effective at concentration ranges lower than those generally found in commercially available artificial "tanning" products.

DETAILED DESCRIPTION OF THE INVENTION

We have found that skin darkening closely resembling the tanning produced by ultraviolet radiation can be duplicated by certain carrier solvent/copper cation systems.

The compounds comprising the active ingredients in the present invention consist of cuprous chloride and either benzyl alcohol or 2,3-dihydroxybenzoic acid in aqueous solution. Cuprous chloride disassociates in water giving $Cu^+$ ions, which are believed to be the active species. This theory is supported by the observation that no enhancement in tanning ability is apparent if solid cuprous chloride is added to a solution already saturated with cuprous chloride. The range of $Cu^+$ ion useful in our invention is from about 0.45 mg/ml to about 0.9 mg/ml, the latter representing a saturated solution. The other active ingredient can be either benzyl alcohol or 2,3-dihydroxybenzoic acid, and is thought to act as a carrier solvent for the $Cu^+$ ion. For use in our invention, the percent of carrier solvent by volume should be between 2% and 4%, the latter representing a saturated solution.

It is preferred that the aqueous solution be saturated with respect to both the cuprous ion and the carrier solvent. As the concentration of active ingredients is decreased, a corresponding decrease will occur in the speed of tanning and in the intensity of color ultimately produced. Depending on how light the individual's skin is before treatment, it is possible to use systems where the concentrations of active ingredients are even lower than those set out above and still produce a slight coloration. The lower limits of 0.45 mg/ml for $Cu^+$ and 2% for carrier solvent represent the point at which there is a distinguishable difference between a treated and an untreated site on the skin of an individual with a light complexion.

In its simplest form, our invention consists of cuprous chloride and either benzyl alcohol or 2,3-dihydroxybenzoic acid in water. If desired, it is also possible to employ our invention in conjunction with a pharmaceutically acceptable dermatologic base. By "dermatologic base" is meant a vehicle or carrier suitable for application to the skin, i.e., for topical or external use.

The dermatologic bases in which our carrier solvent/cation sytems may be employed include: hydroalcoholic solutions, i.e. mixtures of water and alcohol containing up to 45% by weight of an alcohol in addition to any benzyl alcohol present; oil-in-water or water-in-oil emulsions including "creams" which are solid emulsions containing suspensions or solutions for external use, and "lotions" which are liquid suspensions or dispersions stabilized by the presence of suspending agents, surface active agents, or both and designed likewise for external application; and gels formed by the use of thickeners such as finely ground kaolin or clay, or other conventional thickeners such as hydroxyethylcellulose which are inert to the other substances in the composition. In addition to the above, cosmetic adjuvants can be added such as emulsifying agents, solvents, preservatives, buffers, perfumes, and bodying materials which confer on the product a desired consistency rendering it adaptable to topical application. It is also possible to dispense the product as an aerosol by packaging it with conventional propellant liquids.

In connection with "lotions", above, it was mentioned that surface active agents could be used in the practice of our invention. If desired, such surface active agents in an amount from about 0.05 to about 1 percent by weight of the composition can be added to the composition of the present invention.

Table I represents surface active agents which are operable in the practice of our invention, but should not be construed as being exclusive since any surface active agent inert to the other ingredients of the compositions may be employed.

TABLE I

| Anionic Surfactants | Nonionic Surfactants |
|---|---|
| fatty taurates | fatty alkanolamides |
| isethionates | alkoxylated amides |
| sarcosinates | amine oxides |
| alkyl- and arylsulfonates | sorbitan esters |
| alkyl-arylsulfonates | phosphate esters |
| napthalenesulfonates | fatty esters |
| sulfosuccinates | glycerol fatty esters |
| fatty ester sulfates | fatty alcohols |
| fatty acid sulfates | alkoxylated alcohols |
| alcohol sulfates | alkoxylated fatty acids |
| ethoxylated alcohol sulfates and sulfonates | |
| ethoxylated alkyl-arylphenol sulfates | |
| ethoxylated fatty sulfates | |
| ether sulfates | |
| alkyl and aryl phosphates | |
| salts of fatty acids | |

| Cationic Surfactants | Ampholytic Surfactants |
|---|---|
| quaternary ammonium salts | betaines |
| alkyl pyridinium salts | sulfobetaines |
| alkyl amine salts | carboxyimidazoles |
| imidazolines | |
| alkyl guanidines | |
| acyl- and alkylpiperazines | |

While artificial tanning systems may be used by persons as a substitute for natural tanning, they may also be used by persons wishing to accelerate color development in the natural tanning process by using an artificial tanning composition in addition to exposing themselves to sunlight or other sources of ultraviolet radiation. Thus, it is of additional advantage to employ a system containing a conventional sunscreen in order to protect the skin from radiation that may produce dermal erythema. Our present invention satisfies that requirement and may be used with a variety of commercially available sunscreens. It is possible to use water soluble sunscreens as well as those having only limited solubility in water by employing a co-solvent such as ethanol in amounts up to 10% by volume in the final composition. In formulating emulsion bases, the sunscreen is added to the phase in which it is soluble. While almost any sunscreen will work, it is necessary in the practice of our invention to insure that no chemical reaction will occur between the particular sunscreen chosen and the tanning solution. The sunscreens of Table II may be employed in amounts from 0.1% to 3.0% by weight of the composition.

TABLE II p-aminobenzoic acid
sodium 2,2-dihydroxy-4,4-dimethoxy-5-sulfobenzophenone
amyl p-dimethylaminobenzoate
2-ethylhexyl p-dimethylaminobenzoate
glyceryl p-aminobenzoate
2-phenylbenzimidazolesulfonic acid
p-methoxycinnamic acid, diethanolamine salt
2-hydroxy-4-methoxybenzophenone
ethylhexyl p-methoxycinnamate
2-ethoxyethyl p-methoxycinnamate The preferred concentration of sunscreen is approximately 0.1% by weight.

As stated previously, it is possible to dispense the product as an aerosol. Suitable propellants for the composition include, for example, hydrocarbons such as n-butane or isobutane present alone or in mixture thereof with propane; and halogenated hydrocarbons such as those sold under the trademark Freon, for example dichlorodifluoromethane, monochlorotrifluoromethane, trichlorotrifluoroethane, dichlorotetrafluoroethane, etc.

The following specific examples are intended to illustrate the nature of this invention without acting as a limitation upon its scope.

EXAMPLE I: AQUEOUS SOLUTION

Excess crystalline, anhydrous cuprous chloride is added with stirring to a previously prepared saturated solution of benzyl alcohol in water. The resulting saturated solution contains approximately 4 grams of benzyl alcohol and 90 mg of cuprous chloride per 100 ml. Within a short time (30 minutes to 2 hours) after applying this solution to the untanned skin, a golden-brown color closely resembling the color of a natural suntan appears. The color produced is not rubbed off by clothing, nor is it affected by normal washing and bathing. Over a period of several days, it gradually fades.

EXAMPLE II: AQUEOUS SOLUTION

| Ingredient | % by Weight |
|---|---|
| 2,3-dihydroxybenzoic acid | 3.0 |
| Cuprous chloride | 0.06 |
| p-methoxycinnamic acid, diethanolamine salt | 1.0 |
| Octylphenoxypolyethoxyethanol (Triton X-100, Rohm & Haas, West Philadelphia, Penn.) | 0.1 |
| Water | q.s to 100 |
| Procedure: Combine ingredients and stir. | |

EXAMPLE III: O/W CREAM

| Ingredient | % by Weight |
|---|---|
| A. Cetyl alcohol | 17.5 |
| Polyoxyethylene (75) sorbitol lanolin derivative (Atlas G-1471, ICI America, Inc., Stamford, Conn.) | 4.0 |
| Sorbitan monolaurate (Arlacel 20, ICI America, Inc., Stamford, Conn.) | 2.5 |
| Polyoxyethylene (20) sorbitan monolaurate (Tween 20, ICI America, Inc., Stamford, Conn.) | 6.0 |
| B. Cuprous chloride | 0.045 |
| Benzyl alcohol | 2.0 |
| Preservative | 0.1 |
| Water | q.s. to 100 |
| Procedure: Combine the ingredients in (A) and heat to 70° C. Prepare mixture (B) and heat to 72° C. Add (B) to (A) with agitation. Stir until cooled to room temperature. | |

EXAMPLE IV: O/W CREAM

| Ingredient | % by Weight |
|---|---|
| A. Stearic acid, triple pressed | 19.0 |
| Isopropyl myristate | 4.0 |
| Polyoxyethylene (40) stearate (Myrj 52, ICI America, Inc., Stamford, Conn.) | 2.0 |
| Polyoxyethylene (20) sorbitan monostearate (Tween 60, ICI America, Inc., Stamford, Conn.) | 8.0 |
| B. p-aminobenzoic acid | 1.0 |
| Cuprous chloride | 0.05 |

-continued

| Ingredient | % by Weight |
|---|---|
| benzyl alcohol | 2.3 |
| Preservative | 0.1 |
| Water | q.s. to 100 |

Procedure: Combine the ingredients in (A) and heat to 70° C. Combine the ingredients in (B) and heat to 72° C. Add (B) and (A) slowly with agitation. Continue agitation without heat until set.

EXAMPLE V: O/W LOTION

| Ingredient | | % by Weight |
|---|---|---|
| A. | Stearic acid, triple pressed | 4.0 |
| | Methyl phenyl polysiloxane (Silicone 556 fluid, Dow Corning Corp., Midland, Mich.) | 1.0 |
| | Isopropyl palmitate | 3.5 |
| B. | Polyoxyethylene (8 moles ethylene oxide) (Polyethylene Glycol 400, Union Carbide Corp., New York, NY) | 3.0 |
| | Cuprous chloride | 0.07 |
| | Benzyl alcohol | 3.0 |
| | Triethanolamine (Used to form TEA soap with stearic acid) | 1.77 |
| | Preservative | 0.1 |
| | Glyceryl-p-aminobenzoate (Escalol 106, Van Dyk & Co., Belleville, NJ) | 2.0 |
| | Water | q.s. to 100 |

Procedure: Combine (A) ingredients and heat to 80° C. Combine (B) ingredients and heat to 80° C. Add (B) to (A) with mixing and continue mixing to room temperature.

EXAMPLE VI: O/W LOTION

| Ingredient | | % by Weight |
|---|---|---|
| A. | Cetyl alcohol | 2.0 |
| | Acetylated ester of ethoxylated lanolin alcohols (10 moles of ethylene oxide) (Solulan 98, American Cholesterol Products, Edison, NJ) | 2.0 |
| | Lanolin alcohols and mineral oil (Amerchol L-101, American Cholesterol Products, Edison, NJ) | 5.0 |
| | Polyoxyethylene (40) stearate (Myrj 52, ICI America, Inc., Stamford, Conn.) | 4.0 |
| | Glycerin | 2.0 |
| B. | Magnesium aluminum silicate (Veegum HV, R.T. Vanderbilt Co., New York, NY) | 1.0 |
| | Cuprous chloride | 0.07 |
| | 2,3-dihydroxybenzoic acid | 3.0 |
| | Preservative | 0.1 |
| | Water | q.s. to 100 |

Procedure: Combine (A) ingredients and heat to 85° C. Combine (B) ingredients and heat to 85° C. Add (B) to (A) with stirring and cool to room temperature.

EXAMPLE VII: AEROSOL FOAM

| Ingredient | | % by Weight |
|---|---|---|
| A. | Stearic acid, triple pressed | 8.0 |
| | Cetyl alcohol | 1.2 |
| | Polyoxyethylene (40) stearate (Myrj 52, ICI America, Inc., Stamford, Conn.) | 3.0 |
| B. | Propylene glycol | 4.0 |
| | Cuprous chloride | 0.07 |
| | Benzyl alcohol | 3.0 |
| | Preservative | 0.1 |
| | Water | q.s. to 100 |

Procedure: Combine (A) ingredients and heat to 70° C. Combine (B) ingredients and heat to 72° C. Add (B) and (A) with mixing and cool to room temperature. Package as aerosol using a ratio of 7 parts of 70/30 blend of Propellants 11/12 to 93 parts of concentrate.

EXAMPLE VIII: AEROSOL SPRAY

| Ingredient | | % by Weight |
|---|---|---|
| A. | Diethylene glycol monostearate (self emulsifying) (Diglycol stearate S.E., Armour Industrial Chemical Co., Chicago, Il.) | 3.0 |
| | Phenyl dimethicone (Silicone 556 fluid, Dow Corning Corp., Midland, Mich.) | 1.0 |
| | Cetyl alcohol | 0.5 |
| | Acetylated lanolin alcohols (Acetulan, American Cholesterol Products, Edison, NJ) | 2.0 |
| B. | Magnesium aluminum silicate (Veegum, R.T. Vanderbilt Co., Inc., New York, NY) | 1.5 |
| | Propylene glycol | 3.0 |
| | Cuprous chloride | 0.07 |
| | Benzyl alcohol | 3.1 |
| | Water | q.s. to 100 |

Procedure: Add the Veegum to water slowly, agitating and continuously until smooth. Add remaining (B) ingredients and heat to 80° C. Combine (A) ingredients and heat to 75° C. Add (B) to (A) with mixing and cool to room temperature.

Packaging: Combine concentrate (90%) with 10% of a 40/60 blend of Propellants 12/114.

EXAMPLE IV: GEL

| Ingredient | | % by Weight |
|---|---|---|
| A. | Hydroxyethylcellulose (Natrosol 250 HR, Hercules, Inc., Wilmington, Del.) | 2.0 |
| B. | Cuprous chloride | 0.08 |
| | Benzyl alcohol | 3.5 |
| | Preservative | 0.1 |
| | Water | q.s. to 100 |

Procedure: Combine (B) ingredients and mix. Add (A) to (B) with mixing and continue until cellulose is hydrated. Let stand overnight.

When applied to the skin, each of the compositions of Examples II–IX will result in the appearance of a golden-brown color closely resembling the color of a natural suntan within 30 minutes to 2 hours after application.

What is claimed is:

1. A skin coloring composition comprising an aqueous dermatologic base containing cuprous chloride and a member of the group consisting of benzyl alcohol and 2,3-dihydroxybenzoic acid, the concentration of said member in water being from 2 percent to 4 percent by volume and of said cuprous chloride in water being from 0.045 percent to 0.09 percent by weight.

2. A composition as described in claim 1 and including a sunscreen, the concentration of said sunscreen being from 0.1 percent to 3.0 percent by weight.

3. A composition as described in claim 1 in which said aqueous dermatologic base is saturated with said cuprous chloride and with said member of the group consisting of benzyl alcohol and 2,3-dihydroxybenzoic acid.

4. A composition as described in claim 1 and including a surfactant, the concentration of said surfactant being from 0.05 percent to 1.0 percent by weight.

5. A method of coloring skin comprising the application of an aqueous dermatologic base containing cuprous chloride and a member of the group consisting of benzyl alcohol and 2,3-dihydroxybenzoic acid, the concentration of said member in water being from 2 percent to 4 percent by volume and of said cuprous chloride to water being from 0.045 percent to 0.09 percent by weight.

6. A method as described in claim 5 in which said aqueous dermatologic base is saturated with said cuprous chloride and with said member of the group consisting of benzyl alcohol and 2,3 dihydroxybenzoic acid.

* * * * *